US007981432B2

(12) United States Patent
Singh et al.

(10) Patent No.: US 7,981,432 B2
(45) Date of Patent: Jul. 19, 2011

(54) PROTEINS WITHIN THE TYPE E BOTULINUM NEUROTOXIN COMPLEX

(75) Inventors: Bal Ram Singh, Dartmouth, MA (US); Zhong Zhang, New Bedford, MA (US)

(73) Assignee: University of Massachusetts, Shrewsbury, MA (US)

( * ) Notice: Subject to any disclaimer, the term of this patent is extended or adjusted under 35 U.S.C. 154(b) by 94 days.

(21) Appl. No.: 12/247,124

(22) Filed: Oct. 7, 2008

(65) Prior Publication Data

US 2009/0149393 A1    Jun. 11, 2009

Related U.S. Application Data (60) Division of application No. 10/766,283, filed on Jan. 27, 2004, now Pat. No. 7,431,935, which is a division of application No. 09/546,136, filed on Apr. 10, 2000, now Pat. No. 6,699,966, which is a continuation of application No. 08/889,354, filed on Jul. 8, 1997, now abandoned.

(60) Provisional application No. 60/021,348, filed on Jul. 8, 1996.

(51) Int. Cl.
*C07K 14/00* (2006.01)
*A61K 38/00* (2006.01)
*A61K 38/43* (2006.01)

(52) U.S. Cl. .................. 424/239.1; 424/236.1; 424/9.1; 512/2; 512/12; 530/350

(58) Field of Classification Search ............... 424/239.1, 424/236.1, 9.1; 514/2, 12; 530/350; 435/252.7
See application file for complete search history.

(56) References Cited

FOREIGN PATENT DOCUMENTS
WO      WO 95/17904        7/1995

OTHER PUBLICATIONS

Babiuk, "Broadening the approaches to developing more effective vaccines," Vaccine, 17:1587-1595 (1999).
DasGupta et al., "Purification and amino acid composition of type E botulinum neurotoxin," Toxicon, 21:535-545 (1983).
East et al., "Conserved structure of genes encoding components of botulinum neurotoxin complex M and the sequence of the gene coding for the nontoxic component in nonproteolytic *Clostridium botulinum* type F," Current Microbiology, 29:69-77 (1994).
Fiock et al., "Studies on immunity to toxins of *Clostridium botulinum*. VII. Purification and detoxification of trypsin-activated type E toxin," J. Bacteriology, 82:66-72 (1961).
Fujii et al., "The complete nucleotide sequence of the gene encoding the nontoxic component of *Clostridium botulinum* type E progenitor toxin," J. General Microbiology, 139:79-86 (1993).
Gimeniz et al., "Simplified purification method for *Clostridium botulinum* type E toxin," App. Environ. Microbio., 53:2827-2830 (1987).
Hauser et al., "Organization of the botulinum neurotoxin C1 gene and its associated non-toxic protein genes in *Clostridium botulinum* C 468," Mol. Gen. Genet, 243:631-640 (1994).
Johnson, "Clostridial toxins as therapeutic agents: benefits of nature's most toxic proteins," Annu. Rev. Microbiol., 53:551-575 (1999).
Kitamura et al., "Significance of 12S toxin of *Clostridium botulinum* type E," J. Bacteriology, 98:1173-1178 (1969).
Molgo et al., "Characterization of the actions of botulinum neurotoxin type E at the rat neuromuscular junction," Acta Physiol Scand, 137:497-501 (1989).
Sakaguchi, "*Colostridum Botulinum* Toxins," Pharmac. Ther., 19:165-194 (1983).
Schmidt et al., "Purification of type E botulinum neurotoxin by high-performance ion exchange chromatography," Analytical Biochem., 156:213-219 (1986).
Simpson et al., "Use of monoclonal antibodies as probes for the structure and biological activity of botulinum neurotoxin," J. Pharm. Exp. Ther., 255(1):227-232 (1990).
Simpson et al., "Botulinum neurotoxin type E: studies on mechanism of action and on structure-activity relationships," J. Pharm. Exp. Ther., 224(1):135-140 (1983).
Singh et al., "Botulinum versus tetanus neurotoxins: why is botulinum neurotoxin but not tetanus neurotoxin a food poison?" Texicon, 33(12):1541-1547 (1995).
Singh et al., "Physicochemical and immunological characterization of the type E botulinum neurotoxin binding protein purified from *Clostridium botulinum*," J. Protein Chemistry, 14(1):7-18 (1995).
Somers et al., "*Clostridium botulinum* types A, B, C1, and E produce proteins with or without hemagglutinating activity: do they share common amino acid sequences and genes?" J. Protein Chemistry, 10(4):415-425 (1991).

*Primary Examiner* — Chih-Min Kam
(74) *Attorney, Agent, or Firm* — Fish & Richardson P.C.

(57) ABSTRACT

The invention features a polypeptide complex synthesized by bacteria of the genus *Clostridia* that contains the serotype E botulinum neurotoxin and five neurotoxin associated polypeptides having molecular weights of about 118, 80, 65, 40, and 18 kDa, respectively. The complex is useful in the treatment of diseases or conditions that are caused by excessive release of acetylcholine from presynaptic nerve terminals.

6 Claims, 5 Drawing Sheets

1
MELKQAFVFEFDENLSSSSGSIHLEKVKQNCSPNYDYFKITFIDGYLYIKNKSGVI
LDKYDLKNVISLVALKRDYLSLSNNKQIKKFKNIKNKHLKNKFNLYVINEDIE
KRITKNGIIEEVILNKMLLSILLGNEENLLQIS-144
(SEQ ID NO:5)

BoNT

C orf22 — HA70 — HA17 — HA33 — NBP — BaNT
mRNA
mRNA
mRNA

A&B

HA17 — HA33 — orf22 — NBP — BaNT
mRNA
mRNA
mRNA

F orf22 — P-47 — NBP — BaNT
mRNA
mRNA
mRNA
mRNA

E

P-70 — P-13 — P-48 — NBP — BaNT
mRNA
mRNA
mRNA
mRNA
mRNA

SEQUENCE LISTING (1) GENERAL INFORMATION:

(iii) NUMBER OF SEQUENCES: 5

(2) INFORMATION FOR SEQ ID NO: 1:

(i) SEQUENCE CHARACTERISTICS:
      (A) LENGTH: 10 amino acids
      (B) TYPE: amino acid -continued

```
        (D) TOPOLOGY: linear (ii) MOLECULE TYPE: peptide (xi) SEQUENCE DESCRIPTION: SEQ ID NO: 1:

Met Lys Gln Ala Phe Val Phe Glu Phe Asp
 1               5                  10

(2) INFORMATION FOR SEQ ID NO: 2:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO: 2:

Met Arg Ile Asn Thr Asn Ile Asn Ser Met
 1               5                  10

(2) INFORMATION FOR SEQ ID NO: 3:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO: 3:

Met Gln Thr Thr Thr Leu Asn Trp Asp Thr
 1               5                  10

(2) INFORMATION FOR SEQ ID NO: 4:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO: 4:

Thr Asn Leu Lys Pro Tyr Ile Ile Tyr Asp
 1               5                  10

(2) INFORMATION FOR SEQ ID NO: 5:

(i) SEQUENCE CHARACTERISTICS:
        (A) LENGTH: 144 amino acids
        (B) TYPE: amino acid
        (D) TOPOLOGY: linear (ii) MOLECULE TYPE: peptide (xi) SEQUENCE DESCRIPTION: SEQ ID NO: 5:

Met Glu Leu Lys Gln Ala Phe Val Phe Glu Phe Asp Glu Asn Leu Ser
 1               5                  10                  15

Ser Ser Ser Gly Ser Ile His Leu Glu Lys Val Lys Gln Asn Cys Ser
                20                  25                  30

Pro Asn Tyr Asp Tyr Phe Lys Ile Thr Phe Ile Asp Gly Tyr Leu Tyr
            35                  40                  45

Ile Lys Asn Lys Ser Gly Val Ile Leu Asp Lys Tyr Asp Leu Lys Asn
       50                  55                  60

Val Ile Ser Leu Val Ala Leu Lys Arg Asp Tyr Leu Ser Leu Ser Leu
65                  70                  75                  80
```

```
Ser Asn Asn Lys Gln Ile Lys Lys Phe Lys Asn Ile Lys Asn Lys His
                85                  90                  95

Leu Lys Asn Lys Phe Asn Leu Tyr Val Ile Asn Glu Asp Ile Glu Lys
            100                 105                 110

Arg Ile Thr Lys Asn Gly Ile Leu Glu Glu Val Ile Leu Asn Lys Met
        115                 120                 125

Leu Leu Ser Ile Leu Leu Gly Asn Glu Glu Asn Leu Leu Gln Ile Ser
    130                 135                 140
```

PROTEINS WITHIN THE TYPE E BOTULINUM NEUROTOXIN COMPLEX

This application is a divisional of U.S. application Ser. No. 10/766,283, filed on Jan. 27, 2004, now U.S. Pat. No. 7,431,935, which is a divisional of U.S. application Ser. No. 09/546,136, filed on Apr. 10, 2000, now U.S. Pat. No. 6,699,966, which is a continuation of U.S. application Ser. No. 08/889,354, filed on Jul. 8, 1997, now abandoned, which claims the benefit of priority from U.S. Provisional Application Ser. No. 60/021,348, filed on Jul. 8, 1996, which are all incorporated herein by reference in their entirety.

STATEMENT AS TO FEDERALLY SPONSORED RESEARCH

This work was supported by grants from the United States Department of Agriculture (94-37201-1167) and the United States Department of Defense (NRL-ERDC-N00014-92-K-2007). The U.S. government may have certain rights in the invention.

BACKGROUND OF THE INVENTION

The present invention relates to novel proteins that form a complex with the type E botulin neurotoxin.

Various strains of the bacterium *Clostridium*, including *C. botulinum*, *C. baratii*, and *C. butyricum*, synthesize different serotypes of the potent neurotoxin botulin, which causes a form of food poisoning known as botulism. *C. botulinum* synthesizes seven different serotypes of botulin, which are designated by the letters A through G. Humans and other animals come into contact with these neurotoxins most frequently by consuming food that is improperly stored in a way that permits growth of anaerobic bacteria. Foods that are typically tainted with botulin include low acid canned meats and vegetables, preserved meats and fish, and pasteurized processed cheese spreads (Fogeding, In Foodborne Microorganisms and Toxins: Developing Methodology, M. D. Pierson and N. Sterns, Eds., Marcel Dekker, Inc., New York, N.Y., 1986; Kautter et al, *J. Food Prot.* 42:784-786, 1979).

Another form of botulism, infant botulism, is thought to be caused by consumption of ubiquitous spores of *C. botulinum* along with food (Simpson, In Botulinum Neurotoxin and Tetanus Toxin, Academic Press, San Diego, Calif., 1989). These spores may colonize the infant intestine, germinate, and produce the neurotoxin. Similarly, spores that gain access to deeply wounded tissue may germinate and produce neurotoxin within the wound.

Once present in the body, botulin neurotoxins cause muscle paralysis by blocking the release of acetylcholine from cholinergic nerve endings (DasGupta et al., Biochemistry and Pharmacology of Botulinum and Tetanus Neurotoxins, In Perspective in Toxicology, A. W. Bernheimer, Ed., Wiley, New York, N.Y., 1977). Death may be caused by paralysis of the respiratory muscles.

The nucleotide sequences of the genes encoding all of the different serotypes of the neurotoxin are known (Binz et al., *J. Biol. Chem.* 265:9153-9158, 1990; Campbell et al., *J. Clin. Microbiol.* 31:2255-2262, 1993; East et al., *FEMS Microbiol. Lett.* 96:225-230, 1992; Hauser et al., *Nucl. Acids Res.* 18:4924, 1990; Whelan et al., *Eur. J. Biochem.,* 204:657-667, 1992; and Whelan et al., *Appl. Environ. Microbiol.* 58:2345-2354, 1992). These genes are coordinately regulated with those encoding proteins that form complexes with the various serotypes of botulin (Fujii et al., *J. Gen. Microbiol.* 139:79-83, 1993; and Nukina et al., In Botulinum and Tetanus Neurotoxins, B. R. DasGupta, Ed., Plenum Press, New York, N.Y., 1993). The A and B type neurotoxins are associated with at least five other proteins, called "neurotoxin binding proteins" or NAPS, while the type E neurotoxin has been found in association with only one other protein (Sugii et al, *Infect. Immunol.* 12:1262-1270, 1975; Sakaguchi, *Pharmac. Ther.* 19:165-194, 1983; Schantz et al., *Microbiol. Rev.* 56:80-99, 1992; and Singh et al., *J. Protein Chem.* 14:7-18, 1995).

The proteins that associate with the type A neurotoxin play a critical role in the food poisoning process by protecting the neurotoxin from the acids and proteolytic enzymes present in the gastrointestinal tract. For example, it is known that the oral toxicity of the intact type A neurotoxin complex is 43,000 times greater than the oral toxicity of isolated and purified type A neurotoxin (Sakaguchi, *Pharmac. Ther.* 19:165-194, 1983). The proteins associated with other serotypes similarly "protect" the neurotoxin, but to a lesser degree.

SUMMARY OF THE INVENTION

The invention is based on the discovery that the type E botulinum toxin exists in a complex that includes the toxin and five other polypeptides termed neurotoxin associated proteins (NAPs). This discovery is contrary to the prior assertions of those in the field, who believed that the toxin was associated with only one other polypeptide, a neurotoxin binding protein (NBP) having a molecular weight of approximately 118 kDa.

Accordingly, the invention features a substantially pure polypeptide complex that includes a *Clostridium botulinum* neurotoxin and more than one *Clostridium botulinum* type E neurotoxin associated polypeptide. The polypeptides of the invention include the newly discovered NAPs, which have molecular weights of approximately 80, 65, 40, and 18 kDa, and substantially pure antibodies that specifically bind to one or more of these polypeptides, or complexes of one or more of the NAPs with type E botulinum toxin, or toxins from other *Clostridium botulinum* serotypes including A, B, C, D, F, and G.

Figure 8:
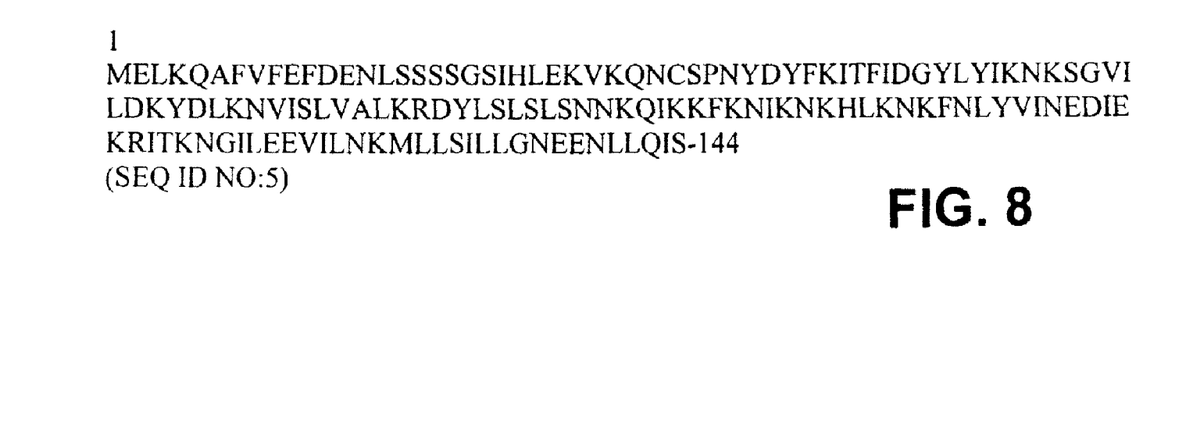
FIG. 8 is a representation of the amino acid sequence of a type E botulin NAP having a molecular weight of approximately 18 kDa (SEQ ID NO:5).

The following peptide sequences have been obtained: (1) MKQAFVFEFD (SEQ ID NO:1), from the 18 kDa polypeptide; (2) MRINTNINSM (SEQ ID NO:2), from the 40 kDa polypeptide; (3) MQTTTLNWDT (SEQ ID NO:3), from the 65 kDa polypeptide; and (4) TNLKPYIIYD (SEQ ID NO:4), from the 80 kDa polypeptide. In addition, the complete amino acid sequence of the 18 kDa polypeptide has been obtained and is shown in FIG. 8 (SEQ ID NO:5).

The compositions of the invention (e.g., the novel NAPs and antibodies that specifically bind to them) can be used to detect the serotype E neurotoxin complex in a sample. For example, one can contact the sample with an antibody that specifically binds a NAP, or with a NAP that binds the neurotoxin itself (as described in the Examples, below, the NAP having an approximate molecular weight of 80 kDa binds directly to the type E neurotoxin) and detect, if present, antibody-bound type E associated polypeptide or NAP-bound type E neurotoxin. The presence of these antibody complexes indicates the presence of serotype E neurotoxin in the sample. The detection methods of the invention can be used to examine virtually any type of sample, including samples of foodstuffs, or biological samples, such as gastrointestinal, blood, or tissue samples obtained from a vertebrate animal.

The novel compositions of the invention also provide the basis for methods of treating patients who suffer from a disease or conditions associated with excessive release of acetylcholine from presynaptic nerve terminals. The patient is treated by administration of a therapeutically effective amount of a polypeptide complex that contains the serotype E neurotoxin (or other serotype toxin) and more than one NAP, e.g., one or more of the 80, 65, 40, and 18 kDa NAPs, and/or the 118 kDa polypeptide. The conditions associated with excessive acetylcholine release include undesirable contractions of smooth or skeletal muscle cells, which can, in turn, cause spasmodic torticollis, essential tremor, spasmodic dysphonia, charley horse, strabismus, blepharospasm, oromandibular dystonia, spasms of the sphincters of the cardiovascular, gastrointestinal, or urinary systems, or tardive dyskinesia. Excessive release of acetylcholine can also cause profuse sweating, lacrimation, or mucous secretion. Patients who could benefit from the methods described herein include those who suffer from spasticity that occurs secondary to another event such as brain ischemia, traumatic injury of the brain or spinal cord, tension headache, or pain (e.g., pain caused by sporting injuries or arthritis).

In addition, the novel compositions of the invention can be formulated as a vaccine and administered to an animal in an amount sufficient to confer a degree of protection against serotype E (or other) neurotoxin.

Administration of a purified neurotoxin complex (e.g., of the type E (or other) neurotoxin and more than one of the new NAPs), as described below, is superior to administration of the neurotoxin alone because, within the complex, the neurotoxin is more stable and thus, longer-lasting. This feature minimizes the frequency of administration and thereby reduces any risk, discomfort, or inconvenience that the patient may experience.

The type E complex is a superior therapeutic agent, relative to the other botulinum serotypes, because the activity of the type E neurotoxin can be enhanced 100-fold by treatment with trypsin, which breaks the bonds between the two polypeptide chains that constitute the neurotoxin. Therefore, application of the type E neurotoxin complex can be controlled by trypsinization, in a way that allows graded release of the neurotoxin from the complex. This unique mechanism provides more controlled and longer-lasting effects than would otherwise be possible.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Contrary to the general understanding in the field, the type E botulinum toxin complex consists in vivo of the neurotoxin, which has a molecular weight of about 150 kDa, and five (not one, as previously believed) polypeptides that form a complex with the neurotoxin. These five polypeptides have molecular weights of approximately 118, 80, 65, 40, and 18 kDa. Those of skill in the art will recognize that the measured or apparent molecular weight of a polypeptide can vary depending, for example, on the number of glycosylated residues, and even on the method used to determine the molecular weight. Accordingly, the measured molecular weights of the NAPs of the invention can vary. For example, the measured molecular weight of the approximately 80 kDa polypeptide can vary between 70 and 90 kDa; the measured molecular weight of the approximately 65 kDa polypeptide can vary between 60 and 70 kDa; the measured molecular weight of the approximately 40 kDa polypeptide can vary between 35 and 45 kDa; and the measured molecular weight of the approximately 18 kDa polypeptide can vary between 15 and 21 kDa.

The novel polypeptides discovered in the type E botulinum neurotoxin complex can be used in a number of ways. First, they can be used to detect the presence of the type E botulin toxin in a sample, such as a food sample or a sample of biological tissue, or to generate antibodies that can be used in analogous detection methods. For example, if a patient is exposed to the neurotoxin, the NAPs and NAP-binding antibodies of the invention provide the means (through direct binding detection systems or antibody-based detection systems) for rapid and reliable diagnosis. The NAPs, in their naturally occurring complex with the type E neurotoxin (or complexed individually or in groups with type E or other neurotoxins), are also useful in treating diseases associated with excessive release of acetylcholine from cholinergic nerve terminals and, in addition, they can be used to generate vaccines for immunization. These uses are described in further detail below.

POLYPEPTIDES OF THE INVENTION

The polypeptides of the invention include NAPs having molecular weights of approximately 80, 65, 40, and 18 kDa (alone or in any combination, particularly in a combination that includes the type E (or other) botulin neurotoxin, and/or the neurotoxin binding protein (NBP) having a molecular weight of approximately 118 kDa), and antibodies that specifically bind to one or more of these NAPs or NAP complexes.

The invention encompasses full-length NAPs as well as fragments that correspond to functional domains of the NAPs (e.g., fragments that bind to polypeptides in the type E botulin complex and help to increase the stability of the neurotoxin in vitro or in vivo, or fragments that are antigenic (i.e., that elicit the production of antibodies)). The NAPs of the invention, and fragments thereof, can have the sequence of a wild-type NAP, or can contain a mutation (including deletions, additions, or substitutions of one or more amino acid residues). Preferably, the mutant polypeptides retain at least 50%, 75%, or at least 95% or more of the biological activity of the corresponding wild-type polypeptide. It is a straightforward matter to compare the biological activities of the mutant and wild-type polypeptides. They can, for example, be used in side-by-side tests for lethality in rodents. If an equivalent number of animals are killed regardless of whether they receive a particular dose of a type E complex containing wild-type or mutant NAPs, the mutant NAPs would be said to retain the biological activity of the wild-type NAPs. If only half as many animals die following administration of a complex containing a mutant NAP, then the mutant would be said to retain half the biological activity of the wild-type NAP. Those of skill in the art will be aware of numerous ways in which biological activities can be fairly compared.

Mutant NAPs that contain a substitution of one or more amino acid residues can be made purposefully or randomly (e.g., by using routine techniques of recombinant DNA engineering or random mutagenesis, respectively). Amino acid substitutions may be purposefully changed to affect the polarity, charge, solubility, hydrophobicity, hydrophilicity, or amphipathic nature of the residues involved. Not only may the mutant polypeptides retain biological activity, this activity could be increased. For example, a mutant NAP could be made to bind with a higher affinity to the type E botulin neurotoxin.

Polypeptides in which the NAPs are fused to an unrelated protein (e.g., a protein that can be easily detected or quantitated) are also considered within the scope of the invention.

The polypeptides of the invention can be purified from a naturally-occurring source, chemically synthesized (e.g., see Creighton, In Proteins: Structures and Molecular Principles, W.H. Freeman & Co., New York, N.Y., 1983), or produced by recombinant DNA technology using techniques well known in the art for expressing nucleic acids. These methods can, for example, be used to construct expression vectors containing a NAP-encoding sequence, and appropriate transcriptional and translational control signals.

"Substantially pure" polypeptides are polypeptides in preparations in which they represent at least 60% by weight of the preparation. When one or more NAPs are present in a complex, for example, in a complex with the type E botulin neurotoxin, a substantially pure preparation will consist of at least 60%, by weight, the polypeptides of the given complex. Preferably, preparations containing one or more NAPs are at least 75%, at least 90%, or even at least 99%, by weight, the polypeptide(s) of interest. Purity can be readily measured by any appropriate method, for example, column chromatography, polyacrylamide gel electrophoresis, or HPLC analysis.

The amino acid sequence of the NAP having a molecular weight of approximately 18 kDa has been determined (FIG. 8; SEQ ID NO:5), and partial sequences are described herein for the NAPs having molecular weights of approximately 80 (SEQ ID NO:4), 65 (SEQ ID NO:3), and 40 kDa (SEQ ID NO:2). It is well within the abilities of those of ordinary skill in the art to obtain additional sequence information from the partial sequences disclosed herein. For example, PCR technology can be used to isolate full length NAP cDNA sequences as follows. First, RNA can be isolated, following standard procedures, from an appropriate cellular or tissue source (e.g., a bacterium of the genus *Clostridia*), and reverse transcribed using an oligonucleotide primer specific for the most 5' end of the amplified fragment. This oligonucleotide primes first strand synthesis. The resulting RNA/DNA hybrid can then be "tailed" with guanines using a standard terminal transferase reaction, and the hybrid can be digested with RNAse H. Second strand synthesis can then be primed with a poly-C primer. The sequence of the amplified fragment can then be obtained using any number of routine procedures.

Production of Antibodies Against the Type E Neurotoxin Associated Proteins

Antibodies that specifically bind to one or more epitopes of a NAP, or fragments or derivatives thereof, are also considered within the scope of the present invention. An antibody is said to "specifically bind" to a polypeptide when it recognizes and binds to that polypeptide, but not to other molecules in a sample (e.g., a biological sample that includes type E neurotoxin associated polypeptides). The antibodies of the invention can be polyclonal, monoclonal, humanized, chimeric, or single chain antibodies, or Fab fragments, F(ab')2 fragments, fragments produced by a Fab expression library, anti-idiotype anti-Id) antibodies, and epitope-binding fragments of any of the types of antibodies listed above.

A variety of standard methods can be used to generate antibodies against the type E neurotoxin associated proteins. For example, the type E neurotoxin associated proteins, either individually or in their complexed forms, can be administered to an animal, such as a rat, mouse, or rabbit, to induce the production of polyclonal antibodies. Alternatively, antigenic fragments of the individual polypeptides can be used to generate polyclonal antibodies. Various adjuvants can be used to increase the immunological response to an antigen, depending on the host species. These adjuvants include Freund's (complete or incomplete) adjuvant, mineral gels such as aluminum hydroxide, surface active substances such as lysolecithin, pluronic polyols, polyanions, peptides, oil emulsions, keyhole limpet hemocyanin, and dinitrophenol. Potentially useful human adjuvants are known to include BCG (bacile Calmette-Guerin) and *Corynebacterium parvum*.

In addition, antibodies according to the invention can be monoclonal antibodies (i.e., antibodies from a homogenous population that recognize a particular antigen) that are generated by using either individual serotype E NAPs, the intact type E complex, or complexes of the neurotoxin with the NBP and any one or more of the new NAPs. Such monoclonal antibodies can be prepared using standard hybridoma technology (see; e.g., Kohler et al., *Nature* 256:495, 1975; Kohler et al., *Eur. J. Immunol.* 6:292, and 6:511, 1976; Hammerling et al., In Monoclonal Antibodies and T Cell Hybridomas, Elsevier, N.Y., 1981; Kruisbeck et al., Hornbeck et al., and Yokoyama, In Current Protocols in Immunology, Vol. 1, New York, John Wiley & Sons, Inc., 1994). Monoclonal antibodies can be of any immunoglobulin class, including the IgG, IgM, IgE, IgA, and IgD classes, and any subclass thereof. The hybridoma producing the mAb of the invention can be cultivated in vitro or in vivo.

In addition, techniques developed for the production of "chimeric antibodies" (Morrison et al., *Proc. Natl. Acad. Sci. USA* 81:6851-7955, 1984; Neuberger et al., *Nature* 312:604-608, 1984; Takeda et al., *Nature* 314:452-454, 1985) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine monoclonal antibody and a human immunoglobulin constant region.

Alternatively, techniques described for the production of single chain antibodies (U.S. Pat. No. 4,946,778; Bird, *Science* 242:423-426, 1988; Huston et al., *Proc. Natl. Acad. Sci. USA* 85:5879-5883, 1988; and Ward et al., *Nature* 334:544-546, 1989) can be adapted to produce single chain antibodies against NAPs. Single chain antibodies are formed by linking the heavy and light chain fragments of the Fv region via an amino acid bridge, resulting in a single chain polypeptide.

Antibody fragments that recognize specific epitopes can also be generated by known techniques. For example, such fragments include, but are not limited to: the F(ab')$_2$ fragments that can be produced by pepsin digestion of the antibody molecule and the Fab fragments that can be generated by reducing the disulfide bridges of the F(ab')$_2$ fragments. Alternatively, Fab expression libraries can be constructed (Huse et al., *Science* 246:1275-1281, 1989) to allow rapid and easy identification of monoclonal Fab fragments with the desired specificity.

The binding specificity and activity of purified anti-type E (or other serotypes) complex antibodies, such as those described above, can be confirmed by testing their ability to interfere with the biological activity of the neurotoxin and/or the complex. This ability can be tested by adding the antibodies to any number of standard in vitro assays in which the release of acetylcholine from presynaptic nerve terminals can be monitored. These assays include preparations of different neuromuscular junctions, such as the mouse phrenic nerve-hemidiaphragm, the mouse plantar nerve-lumbrical muscle, and chick ciliary ganglion-iris muscle preparations (Bandyopadhyay et al., *J. Biol. Chem.* 262:2660-2663, 1987); Bittner et al., *J. Biol. Chem.* 264:10354-10360, 1989; Clark et al., *J. Neurosci. Methods* 19:285-295, 1987; and Lomneth et al., *Neurosci. Lett.*, 113:211-216, 1990). The binding specificity and activity of any given antibody is tested by determining whether that antibody effectively blocks the action of type E neurotoxin complex applied at the neuromuscular junction.

Polypeptide-Based Detection Systems for Type E Neurotoxin Associated Proteins

The NAPs described herein have a variety of uses, including the detection of type E neurotoxin. The type A neurotoxin remains associated with its protein complex both in bacterial culture medium and in natural cases of food poisoning (Sakaguchi, *Pharmac. Ther.* 19:165-194, 1983). Given this evidence, it is likely that the 118 kDa binding protein and the other four, lower molecular weight members of the type E complex also remain associated with the cognate toxin in vitro and in vivo. In addition, neurotoxin associated proteins have been shown to be more immunogenic than the neurotoxin itself (Singh et al., *Toxicon* 34:267-275, 1996).

Antibodies generated against any one of the NAPs or combinations thereof can also be used to detect the type E neurotoxin complex using various standard methods. For example, the antibodies can be used with a fiber optic-based biosensor, as described herein, which uses an evanescent wave from a tapered optical fiber for signal discrimination. This antibody-based "sandwich" immunoassay detection system can detect botulinum toxin much more quickly than any method currently available, but other immunoassay methods can be used. The actual signal collection period with the biosensor is less than one minute. Detection is accomplished using a two-step sandwich immunoassay. Antibody-bound optical fibers are incubated in a solution of type E complex, and a signal is generated when th fiber-bound complex binds a fluorescently labeled antibody (see, Ogert et al., *Anal. Biochem.* 205:306-312, 1992; and Singh et al, In Natural Toxins II, B. R. Singh and A. Tu, Eds., Plenum Press, pp. 498-508, 1996).

One of the problems historically associated with sandwich immunoassays is that the first antibody (here, the antibody bound to the optical fiber) and the second antibody (here, the antibody added to detect the fiber-bound complex), compete for the same epitope on the neurotoxin. To circumvent this problem, two antibodies can be used. The first specifically binds to one portion of the neurotoxin or one NAP of the type E complex, which will be attached to the fiber, and a second specifically binds to either a second portion of the neurotoxin or a second member of the polypeptide complex, which would specifically recognize the fiber-bound complex.

Any polypeptide (be it a NAP or an antibody of the invention) can be detectably labeled to facilitate the detection of the type E botulin complex. For example, the polypeptides can be conjugated with a radio-opaque or other appropriate compound, such as a fluorescent compound, that can be brought into contact with a sample that may contain the botulin complex. Alternatively, the polypeptide can be linked to an enzyme and used in an enzyme immunoassay (EIA; Voller et al. *J. Clin. Pathol.* 31:507-520, 1978; Butler, *Methods Enzymol.* 73:482-523, 1981). The enzyme that is bound to the antibody will react with an appropriate substrate, e.g., a chromogenic substrate, in such a manner as to produce a chemical moiety that can be detected, for example, by spectrophotometric, fluorimetric, or visual means. Enzymes that can be used to detectably label a polypeptide include malate dehydrogenase, staphylococcal nuclease, delta-5-steroid isomerase, yeast alcohol dehydrogenase, beta-galactosidase, alkaline phosphatase, ribonuclease, and urease.

Preparation and Administration of A Neurotoxin Vaccine

The invention also includes a vaccine composition containing a type E (or other serotype) neurotoxin and more than one type E neurotoxin associated polypeptide (or immunogenic fragment or derivative thereof) and a pharmaceutically acceptable diluent or carrier, such as phosphate buffered saline or a bicarbonate solution (e.g., 0.24 M NaHCO$_3$). The carriers and diluents used in the invention are selected on the basis of the mode and route of administration, and standard pharmaceutical practice. Suitable pharmaceutical carriers and diluents, as well as pharmaceutical necessities for their use, are described in Remington's Pharmaceutical Sciences. An adjuvant, for example, a cholera toxin, *Escherichia coli* heat-labile enterotoxin (LT), or a fragment or derivative thereof having adjuvant activity, may also be included in the vaccine composition of the invention.

Skilled artisans can obtain further guidance in the preparation of a vaccine for type E neurotoxin complex in Singh et al. (*Toxicon* 27:403-410, 1990). Briefly, approximately 1.5 mg of the type E complex is added to approximately 10 ml of 0.05 M sodium citrate buffer (pH 5.5) and dialyzed against 0.39% formaldehyde at 30° C. for 7 days. The formaldehyde-containing buffer is replaced every day with fresh buffer solution. The detoxified neurotoxin (toxoid or vaccine) is dialyzed against 0.1 M sodium phosphate buffer (pH 7.4) without formaldehyde for two days with several changes of buffer.

The amount of vaccine administered will depend, for example, on the particular vaccine antigen, whether an adjuvant is co-administered with the antigen, the type of adjuvant co-administered, the mode and frequency of administration, and the desired effect (e.g., protection or treatment), as can be determined by one skilled in the art. In general, the vaccine antigens of the invention are administered in amounts ranging between, for example, 1 pg and 100 mg. If adjuvants are administered with the vaccines, amounts of the polypeptide vaccine ranging between, for example, 1 ng and 1 mg can be used. Administration is repeated as necessary, as can be determined by one skilled in the art. For example, a priming dose can be followed by three booster doses at weekly intervals.

Treatment with Polypeptides in the Type E Neurotoxin Complex

Any disease or discomfort associated with an exaggerated release of acetylcholine from a presynaptic nerve terminal can be treated with the purified or isolated type E botulinum neurotoxin complex described herein, or with complexes formed of other serotype toxins combined with one or more of the NAPS described herein. Those of skill in the art are aware of the normal parameters for acetylcholine release and of the normal range of physiological function that is produced when an appropriate amount of this neurotransmitter is released onto a muscle from adjacent nerve terminals. An exaggerated release of acetylcholine would be any level of release that exceeds the normal parameters and causes aberrant physiological function. The diseases or conditions associated with an exaggerated release of acetylcholine can involve spasms of either smooth or skeletal muscle cells. More specifically, these diseases or conditions include spasmodic torticollis, essential tremor, spasmodic dysphonia, charley horse, strabismus, blepharospasm, oromandibular dystonia, spasms of the sphincters of the cardiovascular, gastrointestinal, or urinary systems, and tardive dyskinesia, which may result from treatment with an anti-psychotic drug such as THORAZINE® or HALDOL®.

For example, an adult male patient suffering from tardive dyskinesia resulting from treatment with an antipsychotic drug can be treated with 50-200 units (defined below) of Botulinum type E complex by direct injection into the facial muscles. Within three days, the symptoms of tardive dyskinesia, i.e., orofacial dyskinesia, athetosis, dystonia, chorea, tics and facial grimacing are markedly reduced.

Spasticity that occurs secondary to brain ischemia, or traumatic injury of the brain or spinal cord, are similarly amenable to treatment.

In instances where the postsynaptic target is a gland, nerve plexus, or ganglion, rather than a muscle, the type E complex can be administered to control profuse sweating, lacrimation, and mucous secretion. For example, an adult male patient with excessive unilateral sweating can be treated by administering 0.01 to 50 units of type E botulinum complex to the gland nerve plexus, ganglion, spinal cord, or central nervous system. Preferably, the nerve plexus or ganglion that malfunctions to produce the excessive sweating is treated directly. Administration of type E neurotoxin complex to the spinal cord or brain, while feasible, may cause general weakness.

Other conditions that can be treated include tension headache and pain caused by sporting injuries or arthritic contractions. If necessary, overactive muscles can be identified with electromyography (EMG).

While it is expected that the methods of the invention will most commonly be applied to human patients, domestic pets (such as dogs and cats) and livestock (such as cows, sheep, and pigs) can also be treated with the compositions described herein.

Administration of Polypeptides within the Type E Neurotoxin Complex

The dose of type E neurotoxin complex administered to a patient will depend generally upon the severity of the condition, the age, weight, sex, and general health of the patient, and the potency of the toxin, which is expressed as a multiple of the $LD_{50}$ value for the mouse.

The dosages used in human therapeutic applications are roughly proportional to the mass of muscle to be treated. Typically, the dose administered to the patient is from about 0.01 to about 1,000 units, for example, about 500 units. A unit is defined as the amount of type E neurotoxin (or type E neurotoxin complex) that kills 50% of a group of mice (typically a group of 18-20 female mice that weigh on average 20 grams). The dosage is adjusted, either in quantity or frequency, to achieve sufficient reduction in acetylcholine release to afford relief from the symptoms of the disease or condition being treated.

Physicians, pharmacologists, and other skilled artisans are able to determine the most therapeutically effective treatment regimen, which will vary from patient to patient. The potency of botulinum toxin and its duration of action means that doses are administered on an infrequent basis. Skilled artisans are also aware that the treatment regimen must be commensurate with questions of safety and the effects produced by the toxin.

Typically, the type E neurotoxin complex is suspended in a physiologically acceptable solution, such as normal saline, and is administered by an intramuscular injection. Prior to injection, careful consideration is given to the anatomy of the muscle group, in an attempt to inject the toxin complex into the area with the highest concentration of neuromuscular junctions. If the muscle mass is not very great, the injection can be performed with extremely fine, hollow, teflon-coated needles and guided by electromyography. The position of the needle in the muscle should be confirmed prior to injection of the toxin, and general anesthesia, local anesthesia, or other sedation may be used at the discretion of the attending physician, according to the age and particular needs of a given patient and the number of sites to be injected.

The invention will be further described in the following examples, which do not limit the scope of the invention described in the claims.

EXAMPLES

Production of Botulinum Toxin by Cell Culture

Generally, to obtain botulinum toxin in large amounts, complexed media containing combinations of meat hydrolysate, casein hydrolysate, yeast autolysate, yeast extract, and glucose supplemented with one or more reducing agents are used (Sakaguchi, *Pharmac. Ther.* 19:165-194, 1983). Vegetables autoclaved in saline also provide an excellent culture medium, supporting toxin production by type A- and type B-producing bacteria to a similar extent as laboratory media. Glucose must be added for type E- and type F-producing bacteria to grow in boiled vegetables (Sugii et al., *J. Food Safety* 1:53-65, 1977). The optimum temperature for toxin production by *C. botulinum* is generally regarded as 20-35° C.

Type E *C. botulinum* Produces a Complex
Including Five Neurotoxin Associated Proteins For this series of experiments, *C. botulinum* type E (available from the American Type Culture Collection, 12301 Parklawn Drive, Rockville, Md., 20852 (U.S.A.); Type E *Clostridium botulinum* Accession Nos. 9564, 17786, 17852, 17854, and 17855) was grown for 4 days in 15 ml cooked meat medium. Stock cultures were prepared according to standard methods and stored at −20° C.

The stock culture was activated at 30° C. for approximately 25 hours and then transferred to a growth medium containing 2.0% Trypticase-peptone, 1.0% glucose, 0.025% sodium thioglycolate (BBL Microbiology Systems, Cockeysville, Md.), and 0.5% yeast extract (Difco) adjusted to pH 6.5. When large culture volumes (8 liters) were used, a 12% glucose solution was autoclaved and added to the broth, which was separately prepared and then autoclaved for 1 hour. The culture was incubated for 60-65 hours, and cells were collected by centrifugation. An extract from the cells was prepared at 20° C. by stirring with 0.2 M phosphate buffer (pH 6.0). The resulting suspension was saturated with $(NH_4)_2SO_4$; 39 g/ml) and stored at 4° C.

DEAE-Sephadex Chromatography

Figure 1:
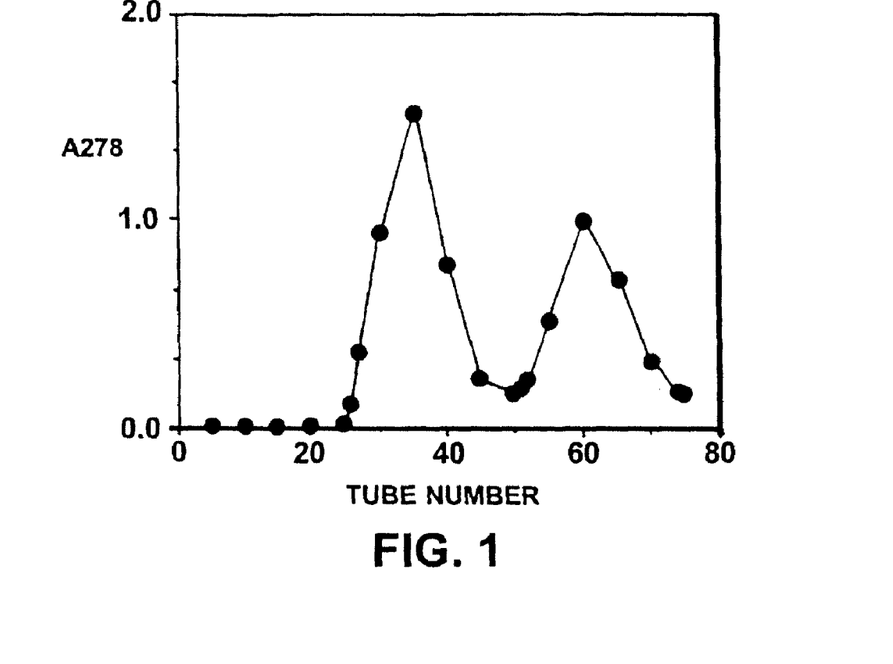
FIG. 1 is an elution profile obtained by applying an extract of E-type producing *C. botulinum* to a DEAE-Sephadex A-50 ion-exchange column (A278 is absorbance at 278 nm).

The crude extract described above was precipitated and redissolved in 35 ml of 0.05 M sodium phosphate buffer (pH 5.5). The resulting solution was clarified by centrifugation and chromatographed on a DEAE-Sephadex A-50 ion-exchange column (Pharmacia). The sample was eluted from the column with 0.05 M sodium citrate at pH 5.5. It is important that the pH of the buffer is maintained at 5.5. The first protein peak (FIG. 1) was pooled as type E complex.

Figure 2:
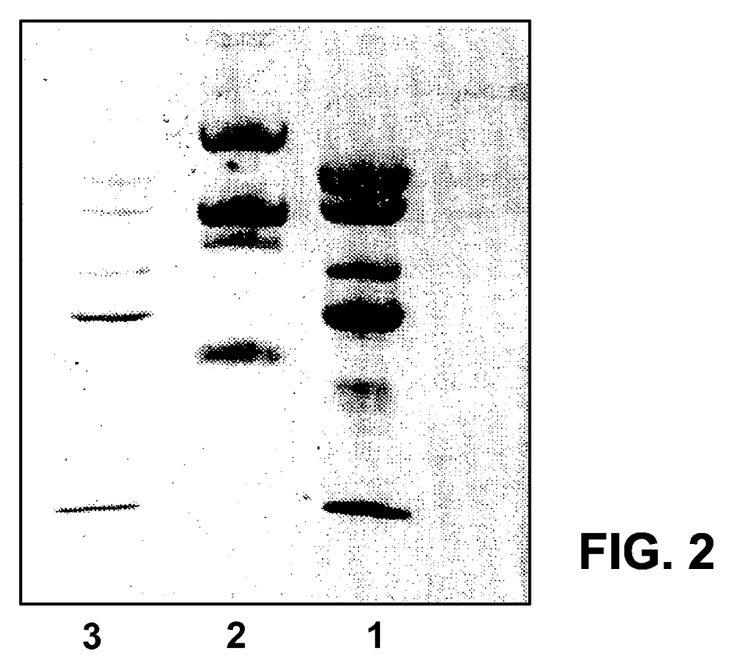
FIG. 2 is a photograph of a polyacrylamide gel. Lane 1 was loaded with the material that eluted in the first peak of FIG. 1. Lane 2 was loaded with molecular weight standards. Lane 3 was loaded with material eluted from a G-200 column (see FIG. 5).

In contrast to previous reports (Sugii et al., *Infect. Immunol.* 12:1262-1270, 1975; Sakaguchi, *Pharmac. Ther.* 19:165-194, 1983; Schantz et al, *Microbiol. Rev.* 56:80-99, 1992; Singh et al., *J. Protein Chem.* 14:7-18, 1995), a total of five different proteins were found in the complex in addition to the 150 kDa type E botulinum neurotoxin. Specifically, the material constituting the first peak of the elution profile described above (and shown in FIG. 1) was analyzed by SDS-polyacrylamide gel electrophoresis. Six proteins, having molecular weights of approximately 150 (the neurotoxin), 118, 80, 65, 40, and 18 kDa, were apparent (FIG. 2).

Size Exclusion Chromatography

Figure 3:
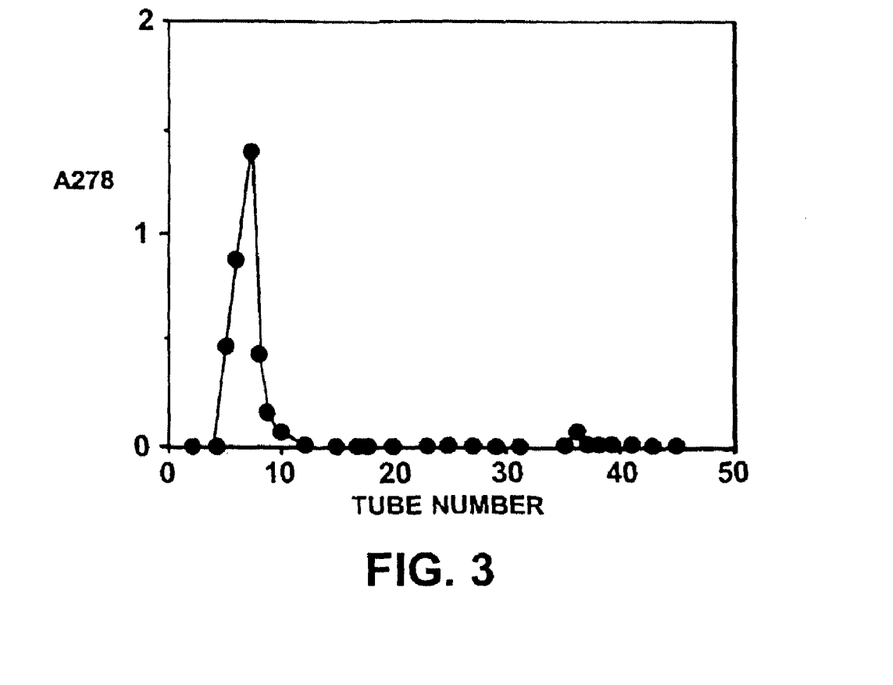
FIG. 3 is an elution profile obtained by applying the type E botulinum neurotoxin complex to a Sephadex G-100 column.
Figure 4:
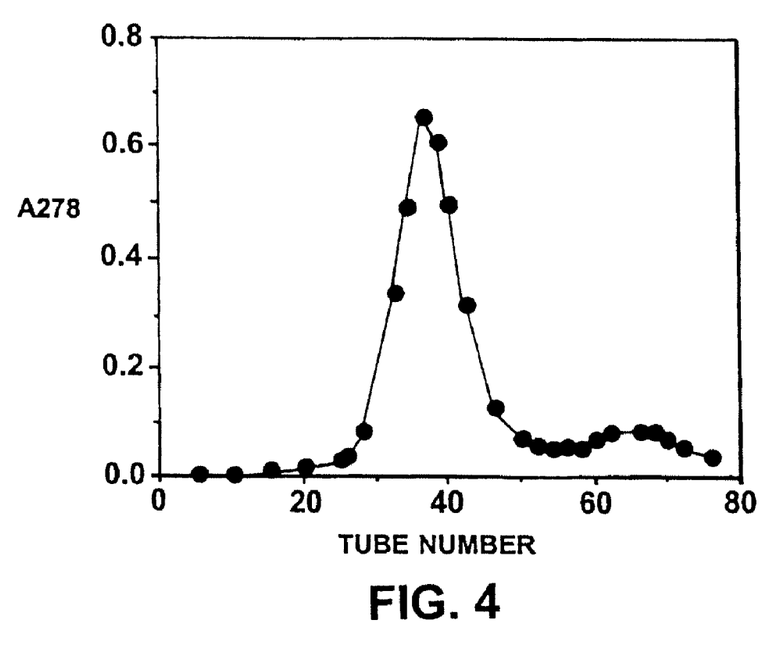
FIG. 4 is an elution profile obtained by applying the type E botulinum neurotoxin complex eluted from a Sephadex G-100 column to a Sephadex G-200 column.

To further confirm the nature of the type E complex, the proteins were analyzed on size exclusion chromatographic columns. The type E complex that eluted from the DEAE Sephadex A-50 column was concentrated to 5 mg/ml and applied to a Sephadex G-100 column (1.8×92 cm or 2.6×82 cm, 0.05 M sodium citrate buffer, pH 5.5). The resulting elution profile revealed one peak in the void volume (FIG. 3). Three of the proteins present are clearly less than the exclusion limit of the column and thus, should elute separately from the void volume. Since this did not occur, and all six proteins continued to elute in one peak, it was concluded that the proteins are bound together in a complex. A similar result was obtained following chromatography on a Sephadex G-200 column (FIG. 4), further confirming that the six proteins form a single complex.

Figure 5:
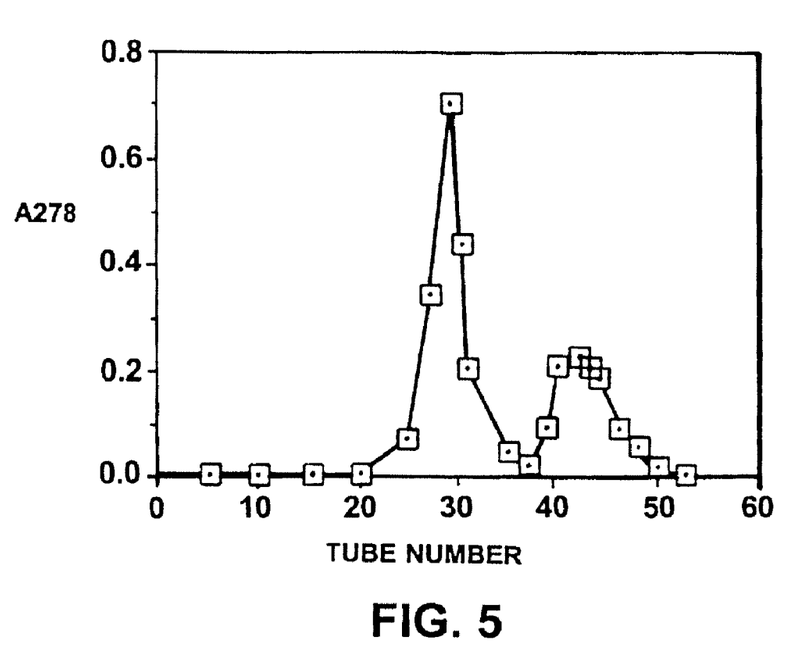
FIG. 5 is an elution profile of the complex formed between type E botulinum neurotoxin and the 80 kDa component of the associated protein complex.
Figure 6:
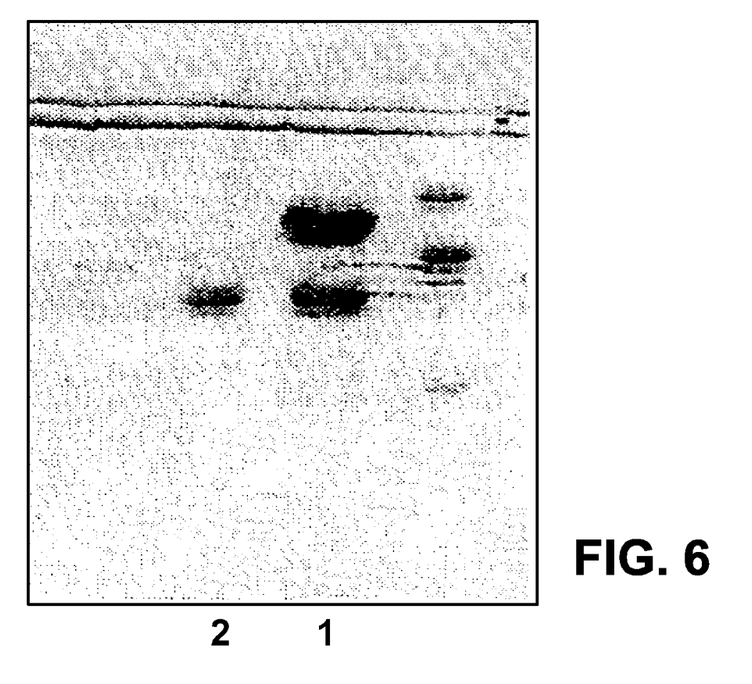
FIG. 6 is a photograph of an SDS-polyacrylamide gel. The material in the first and second peaks of the elution profile shown in FIG. 5 was electrophoresed in lanes 1 and 2, respectively.

One of the neurotoxin associated proteins in the type E complex, the 80 kDa protein, was purified and studied for its ability to re-form a complex with pure type E neurotoxin. After combining the 150 kDa neurotoxin and the 80 kDa associated protein, the elution profile obtained from a Sephadex G-200 column revealed a major peak containing both the 80 kDa protein and the type E neurotoxin, and a minor peak containing excess uncomplexed 80 kDa protein (FIG. 5). The material eluted in each of the two peaks was electrophoresed on an SDS-polyacrylamide gel (FIG. 6), which confirmed the content of the protein(s) in each peak.

The 80 kDa Neurotoxin Associated Protein Specifically Binds Type E Neurotoxin

A kinetic binding study performed with an optical fiber-based biosensor revealed that the type E neurotoxin could bind directly to the 80 kDa type E neurotoxin associated protein, rather than associate indirectly with the neurotoxin via another polypeptide in the complex. The 80 kDa polypeptide was tested for its ability to bind directly to the neurotoxin at pH 7.5 and at pH 5.7. The type E botulinum neurotoxin was first immobilized, and the purified 80 kDa NAP was labeled with TRITC (Tetramethyl-rhodamine-isothiocyanate; Molecular Probes, Eugene, Oreg.) as described in Ogert et al. (*Anal. Biochem.* 205:306-312, 1992), except that unreacted TRITC was removed by dialysis, rather than gel filtration. The binding experiments were carried out by blocking the exposed sites on the optical fiber with 2% BSA (at room temperature) and incubating them with TRITC-labeled 80 kDa polypeptide (5 mg/ml) that had been equilibrated with phosphate buffered saline (PBS; at pH 5.7 or pH 7.5). The initial rate of binding was calculated based on the signal increase within the first 60 seconds.

Subsequent polypeptide binding rates at pH 7.5 and 5.7 were 4.01 and 8.42 μV/minute, respectively, suggesting that the interaction between the neurotoxin and the 80 kDa polypeptide is significant at pH 7.5, and considerably higher at pH 5.7. Therefore, the 80 kDa polypeptide could play a role in protecting the type E neurotoxin from the acidic conditions present in the gastrointestinal tract.

These results are consistent with the known behavior of the botulinum neurotoxin complex, which dissociates at alkaline pH levels. Thus, the associated binding polypeptides can be used as a specific binding partner to "capture," and thereby detect, the neurotoxin. This method would effectively detect the neurotoxin wherever it exists, to at least some degree, free from the complex or, at least, free from the 80 kDa neurotoxin binding protein. The 80 kDa NAP also complexes with Type A neurotoxin.

Sequence Analysis of Proteins in the Type E Neurotoxin Complex

Partial amino acid sequences of the novel polypeptides in the serotype E neurotoxin complex were obtained as follows. Approximately 10 picomoles of the purified type E neurotoxin complex were dissolved in a buffer consisting of 0.5 M sucrose, 15% SDS (sodium dodecyl sulfate), 312.5 mM Tris, and 10 mM EDTA, and electrophoresed on a 12.5% SDS-acrylamide gel using a Mini-PROTEAN II™ electrophoresis cell (Bio-Rad Laboratories, Hercules, Calif.). The electrophoresis was performed in running buffer (2 g/L Tris base, 14.4 g/L glycine, 1 g/L SDS and 0.1 mM sodium thioglycolate, pH 8.3) under a constant voltage (200 V). The protein was then electrotransferred from the gel to a PVDF membrane in a Twobin buffer (25 mM Tris, 192 mM glycine and 20% methanol) using a Mini Trans-Blot electrophoretic transfer Cell™ (Bio-Rad Laboratories, hercules, Calif.). The transfer was carried out overnight at 60 volts in an ice bath. To visualize the protein bands, the membrane was stained with 0.025% Coomassie Blue R250 in 40% methanol and destained with 50% methanol. The proteins bound to the PVDF membranes were sequenced at Baylor College of Medicine (Houston, Tex.) using Applied Biosystem Model 473A protein Sequencer™ (Foster City, Calif.).

The following peptide sequences were obtained: (1) MKQAFVFEFD (SEQ ID NO: 1), from the 18 kDa protein; (2) MRINTNINSM (SEQ ID NO:2), from the 40 kDa protein; (3) MQTTTLNWDT (SEQ ID NO:3), from the 65 kDa protein; and (4) TNLKPYIIYD (SEQ ID NO:4), from the 80 kDa protein. These sequences were compared with those of known proteins associated with neurotoxin types A, B, and C. This analysis failed to reveal any regions of homology with the type A associated proteins of *C. botulinum*.

Genomic Organization

Figure 9:
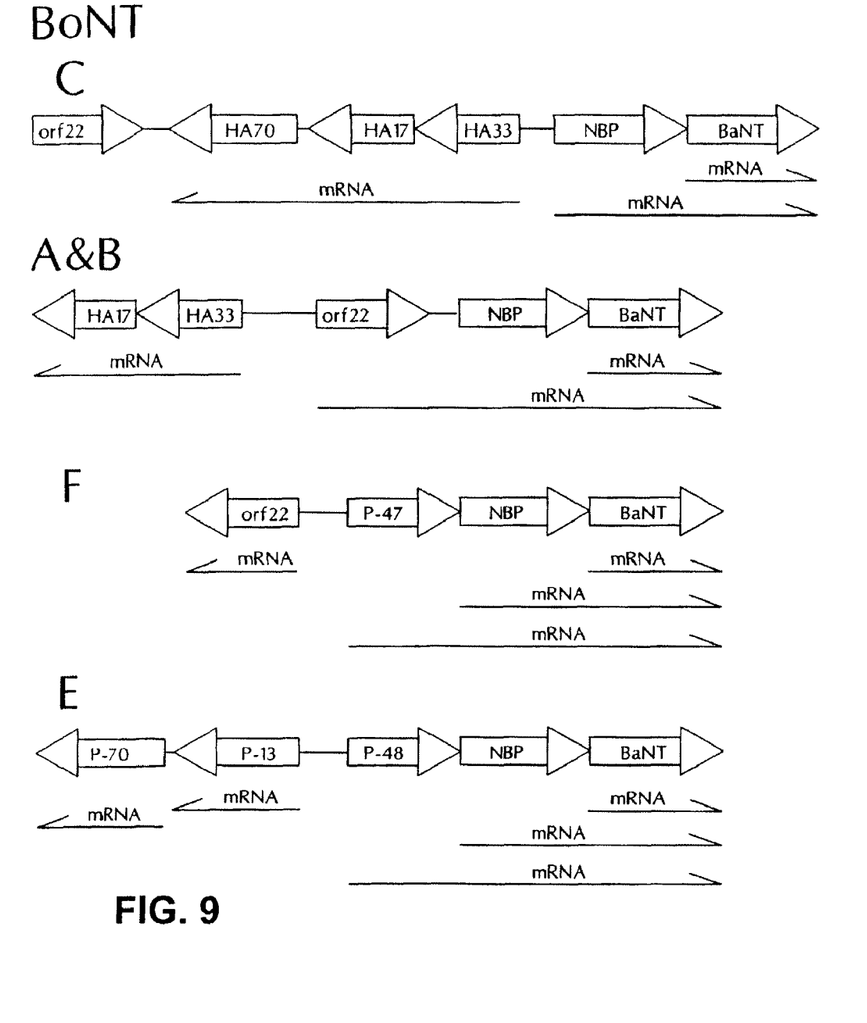
FIG. 9 is a schematic diagram of the genomic organization of *C. botulinum* neurotoxin serotypes C, A and B, F, and E.

The genomic organization of NAPs of type E *C. botulinum* was investigated using oligonucleotide primers having sequences complementary to the N-terminal amino acid sequences. Using combinations of sense and antisense primers (the sequences of which were derived from the amino acid sequences shown in SEQ ID NOs: 1-4 using standard techniques) in a conventional polymerase chain reaction (where chromosomal DNA from bacteria of the genus *Clostridia* served as the template), the topography of the 18 and 80 kDa NAPs were revealed. Both of these genes are transcribed in the opposite direction to that of the neurotoxin and NBP (i.e., the 118 kDa neurotoxin binding protein) genes (FIG. 9). In addition, there is an open reading frame between the NBP and the 18 kDa NAP that has the same transcriptional direction as the NBP. This protein sequence did not match with any of the proteins that have been identified as NAPs of type E *C. botulinum*. In addition to revealing the orientation of various NAP-encoding genes, these experiments revealed that the genes are clustered together within the genome.

Analysis of Type E Neurotoxin
Complex by Light Scattering

To characterize the type E neurotoxin complex as a whole, light scattering experiments were performed on material purified by DEAE-Sephadex A-50 chromatography (1.5 mg/ml). Analysis was performed on a Malvern 4700 PCS Autosizer System (Malvern Instruments Inc.) equipped with an eight-bit, 136 channel correlator capable of variable time expansion. The laser light source was model INNOVA 70-5 argon laser (Coherent, Calif.). A 514.5 nm line was employed in single operation mode with 1.0 watt power output.

Figure 7:
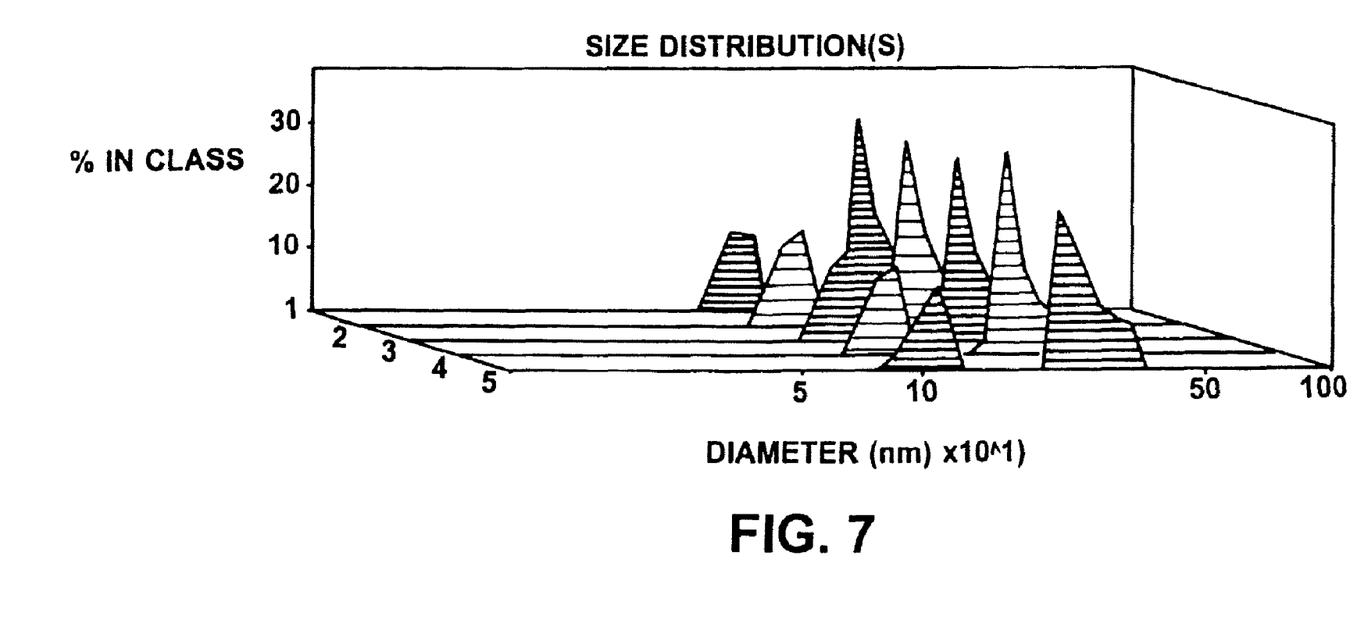
FIG. 7 is a three-dimensional plot generated by light scattering analysis of the type E botulinum complex. The first and second series of peaks were generated with 105 nm and 225 nm diameter particles, respectively.

Initial results from light scattering experiments suggested that the complex exists in two forms, as 600 and 2000 kDa molecular weight species (FIG. 7). The combined molecular weight of the proteins in the type E neurotoxin complex observed on polyacrylamide gels is 468 kDa. The difference between these two predicted sizes could be due either to variation in the folding of the complex or to the existence of oligomeric forms of some of the proteins in the complex.

NAPs Protect the Toxic Activity of Botulin Neurotoxin from Heat

To investigate the role of NAPs in protecting the type E botulin complex from heat, the neurotoxin alone and the intact complex were each heated to 60° C. for 15 minutes, then cooled, and incubated with "cracked" PC12 cells that had been grown in tritiated norepinephrine and stimulated to release norepinephrine by calcium. The term "cracked" is used to describe cells that have been treated with a mechanical device so that their integrity is somewhat disrupted; this technique is described in Lomneth et al., *J. Neurochem.* 57:1413-1421 (1991). The percentage of norepinephrine released into the culture medium was then assessed, because the toxin blocks release of norepinephrine from the cracked cells.

In control experiments, the neurotoxin alone and the intact complex were each incubated with cracked PC12 cells, but not subjected to the 60° C. heat treatment. The control botulin neurotoxin complex (i.e., a complex that had not been heat-treated) reduced the percentage of norepinephrine release from a normal 56.1±0.8% in buffer-treated (no complex, no toxin) cells, to 22.5±0.3% in cells treated by the neurotoxin complex at a final concentration of 50 μg/ml.

In spite of heat treatment (and potential denaturation), the heat-treated complex, at the same concentration of 50 μg/ml, was still able to block, i.e., reduce, the percentage of norepinephrine release to 34.1±0.9%. The type E neurotoxin, when not heated and used alone (i.e., without NAPs) blocked (or reduced) the percentage of norepinephrine release to 21.0±0.6% at 50 μg/ml, whereas heat-treated neurotoxin was not able to substantially block the norepinephrine release (the percent of norepinephrine released was 51.9±1.9%). These data clearly suggest that the presence of NAPs is effective in providing functional stability to the type E botulinum complex.

To determine whether the NAPs provided protection to the botulin complex by preventing heat-induced unfolding of polypeptides in the complex, or by assisting in proper refolding of heated toxin, the heat-induced unfolding of purified neurotoxin and the neurotoxin complex were analyzed by monitoring their circular dichroism (CD) signal at 222 nm. This method has been used successfully to monitor unfolding of proteins (see, e.g., Fahnestock et al., *Science* 258:1658-1662, 1992; and Lehrer and Qian, *J. Biol. Chem.* 265:1134-1138, 1990). The midpoint unfolding temperature (Tm) for the neurotoxin was 54° C. whereas the Tm for the large (new) type E complex was 70° C. The Tm for a neurotoxin complex consisting of the 118 kDa NBP and the type E botulin neurotoxin is between these two values (Sakaguchi, *Pharmac. Ther.* 19:165-194, 1983; Singh et al., *J. Protein Chem.* 14:7-18, 1995). These observations clearly indicate that the loss of type E botulin neurotoxin activity after heating at 60° C. is due to the unfolding of the toxin, whereas no such unfolding occurs in the presence of NAPs.

An observation made while conducting this set of experiments was that the type E botulinum complex is equally (or more) effective in blocking the neurotransmitter release from PC12 cells compared to the pure neurotoxin (without NAPs), although the total effective concentration of the neurotoxin in the complex was only about a third of the pure toxin concentration (111 nM vs. 333 nM). This suggests that the NAPs actually activate the neurotoxin, which would be consistent with our hypothesis that the folding of the type E complex can be altered by NAPs.

Other Embodiments

It is to be understood that while the invention has been described in conjunction with the detailed description thereof, that the foregoing description is intended to illustrate and not limit the scope of the invention, which is defined by the scope of the appended claims. Other aspects, advantages, and modifications are within the scope of the following claims.

What is claimed is:

1. A method of treating a patient who is suffering from spasticity occurring secondary to brain ischemia, or traumatic injury of the brain or spinal cord, the method comprising administering to the patient a therapeutically effective amount of a composition comprising a substantially pure polypeptide complex comprising a *Clostridium botulinum* neurotoxin and one or more *Clostridium botulinum* type E neurotoxin associated polypeptides selected from the group consisting of a polypeptide comprising the amino acid sequence of SEQ ID NO:4, a polypeptide comprising the amino acid sequence of SEQ ID NO:3, a polypeptide comprising the amino acid sequence of SEQ ID NO:2, a polypeptide comprising the amino acid sequence of SEQ ID NO:1, and a polypeptide comprising the amino acid sequence of SEQ ID NO:5, to reduce spasticity in the patient.

2. The method of claim 1, wherein the neurotoxin associated polypeptide comprises the amino acid sequence of SEQ ID NO:4.

3. The method of claim 1, wherein the neurotoxin associated polypeptide comprises the amino acid sequence of SEQ ID NO:3.

4. The method of claim 1, wherein the neurotoxin associated polypeptide comprises the amino acid sequence of SEQ ID NO:2.

5. The method of claim 1, wherein the neurotoxin associated polypeptide comprises the amino acid sequence of SEQ ID NO:1.

6. The method of claim 1, wherein the neurotoxin associated polypeptide comprises the amino acid sequence of SEQ ID NO:5.

* * * * *

UNITED STATES PATENT AND TRADEMARK OFFICE
CERTIFICATE OF CORRECTION

| | | |
|---|---|---|
| PATENT NO. | : 7,981,432 B2 | Page 1 of 1 |
| APPLICATION NO. | : 12/247124 | |
| DATED | : July 19, 2011 | |
| INVENTOR(S) | : Bal Ram Singh | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 0 days.

Signed and Sealed this
Thirteenth Day of March, 2012

David J. Kappos
*Director of the United States Patent and Trademark Office*